(12) United States Patent
Cho

(10) Patent No.: US 8,992,217 B2
(45) Date of Patent: Mar. 31, 2015

(54) APPARATUS AND METHOD FOR USE IN CREATING DENTAL PROSTHETICS

(71) Applicant: David Cho, Citrus Heights, CA (US)

(72) Inventor: David Cho, Citrus Heights, CA (US)

(*) Notice: Subject to any disclaimer, the term of this patent is extended or adjusted under 35 U.S.C. 154(b) by 0 days.

(21) Appl. No.: 13/670,300

(22) Filed: Nov. 6, 2012

(65) Prior Publication Data

US 2013/0084538 A1 Apr. 4, 2013

Related U.S. Application Data

(63) Continuation-in-part of application No. 13/252,013, filed on Oct. 3, 2011.

(51) Int. Cl.
*A61C 19/04* (2006.01)
*A61C 19/045* (2006.01)
*A61B 5/107* (2006.01)
*A61B 5/00* (2006.01)

(52) U.S. Cl.
CPC .............. *A61C 19/045* (2013.01); *A61B 5/1077* (2013.01); *A61B 5/1079* (2013.01); *A61B 5/4542* (2013.01); *A61B 5/4547* (2013.01)
USPC ........................................................ 433/68

(58) Field of Classification Search
CPC ........ A61C 9/00; A61C 9/0053; A61C 11/02; A61C 11/06; A61C 11/08; A61C 13/00; A61C 13/0004; A61C 13/0006; A61C 13/34; A61C 19/04; A61C 19/045; A61C 19/05; A61B 5/1077; A61B 5/1079; A61B 5/4542; A61B 5/4547
USPC ................ 433/55–63, 65, 68–73, 196, 199.1, 433/201.1, 202.1, 203.1, 214, 215, 218, 433/223; 600/587, 590; 396/16
See application file for complete search history.

(56) References Cited

U.S. PATENT DOCUMENTS

| | | | |
|---|---|---|---|
| 1,662,670 A | 3/1928 | Harter | |
| 3,514,606 A | 5/1970 | Rabey | |
| 3,614,950 A | 10/1971 | Rabey | |
| 3,866,323 A * | 2/1975 | Granger | .......................... 433/73 |
| 5,078,600 A | 1/1992 | Austin | |
| 5,738,515 A | 4/1998 | Leever | |
| 6,261,248 B1 * | 7/2001 | Takaishi et al. | ............... 600/590 |
| 2008/0187882 A1 | 8/2008 | Margossian | |
| 2010/0009317 A1 * | 1/2010 | Wiedmann | ................. 433/202.1 |
| 2013/0084537 A1 | 4/2013 | Cho | |

OTHER PUBLICATIONS

Office Action dated May 7, 2012 in parent application: U.S. Appl. No. 13/252,013.

* cited by examiner

*Primary Examiner* — Cris L Rodriguez
*Assistant Examiner* — Justin O'Donnell
(74) *Attorney, Agent, or Firm* — Innovation Counsel LLP

(57) ABSTRACT

An apparatus and method for creating dental prosthetics is provided. The apparatus includes a base, an ear mount portion for making contact with a patient's head such that the patient's temporomandibular joints are maintained in a fixed level position relative to the base, a chin mount portion for making contact with the patient's chin and nose bridge such that the chin mount portion maintains the patient's head in a perpendicular orientation relative to the base, a bite fork portion including a bite fork which may be inserted into the patient's mouth for the purpose of obtaining the patient's bite registration information, and a camera mount portion including a camera oriented toward the patient's face.

14 Claims, 10 Drawing Sheets

APPARATUS AND METHOD FOR USE IN CREATING DENTAL PROSTHETICS

CROSS-REFERENCE TO RELATED APPLICATIONS

This application is a continuation-in-part application of application Ser. No. 13/252,013, filed on Oct. 3, 2011, the entire contents of which are hereby incorporated herein by reference.

TECHNICAL FIELD

The present disclosure is related to an apparatus and method for use in creating dental prosthetics.

DESCRIPTION OF THE RELATED ART

The typical process of creating dental prosthetics involves the dental practitioner taking impressions of a patient's upper and lower jaws and then making models of the patient's jaws (for example, out of plaster) which are sent to the dental lab for use in preparing the necessary prostheses. Dental labs utilize dental articulators to mount these dental models and to position the models to approximate the actual positioning of the patient's upper and lower jaws relative to the patient's temporomandibular joint (TMJ). Once mounted, the dental lab is able to use the models as a guide to create and prepare the required prostheses in the proper size and shape prior to actual implantation in the patient's jaws.

In order to accurately mount the dental models to the articulator, it is necessary for the dental practitioner also to obtain bite registration information from the patient to record the proper spatial orientation of the patient's jaws in relation to the TMJ. The patient's bite registration is usually obtained through the use of a device comprising a facebow with an attached bite fork. The facebow portion is usually designed to contact the patient's two ear canals and nose so as to be positioned approximately parallel to the eye-ear plane, and the bite fork can be adjusted to fit the patient's bite. Once the patient's bite registration has been established, the bite fork is fixed in position relative to the facebow, and some or all of the facebow and bite fork device is sent to the dental lab. The device is then mounted to the articulator in order to physically guide the placement of the dental models on the articulator in the proper spatial orientation.

This method has several disadvantages. First, the facebows in common use today require careful manual application by the dental practitioner of the facebow to the patient's face to accurately record the patient's bite registration, and thus these facebows are prone to provide inaccurate bite registration information to the dental lab.

Second, because articulators from different manufacturers vary in size and structure, few facebows, if any, are compatible with all articulators. As articulators are generally quite expensive, it is costly for a dental lab to maintain different articulators to be able to use different facebows that may be supplied by dental practitioners.

Third, where most or all of the patient's teeth must be replaced by prostheses, such as in the event of a full mouth restoration, the above-described process does not provide sufficient information or guidance to the dental lab regarding the proper appearance and proportions of the dental prostheses to be prepared in relation to the patient's face, and thus the appearance of the prostheses is almost entirely dependent on the technique and preferences of the individual dental lab technician. As a result, it is difficult without repeated and costly trial-and-error steps to ensure that a finished prosthesis has the correct appearance and proportions when applied to the patient's face.

SUMMARY OF THE INVENTION

An apparatus and a method for use in creating dental prosthetics that addresses the problems discussed above is described herein.

Consistent with some embodiments, there is provided an apparatus that permits the measurement of certain patient information for use with a variety of dental articulators to prepare dental prosthetics, including recording a patient's bite registration, measuring the spatial positioning of a patient's occlusal plane, and recording the patient's facial features in a manner consistent from patient to patient.

Consistent with some embodiments, there is also provided a method of preparing dental prostheses is described that utilizes certain data regarding the patient's facial features to assist in the preparation of dental prostheses that have the proper proportion, size and appearance in relation to the patient's face.

DETAILED DESCRIPTION OF THE EMBODIMENTS

Figure 1:
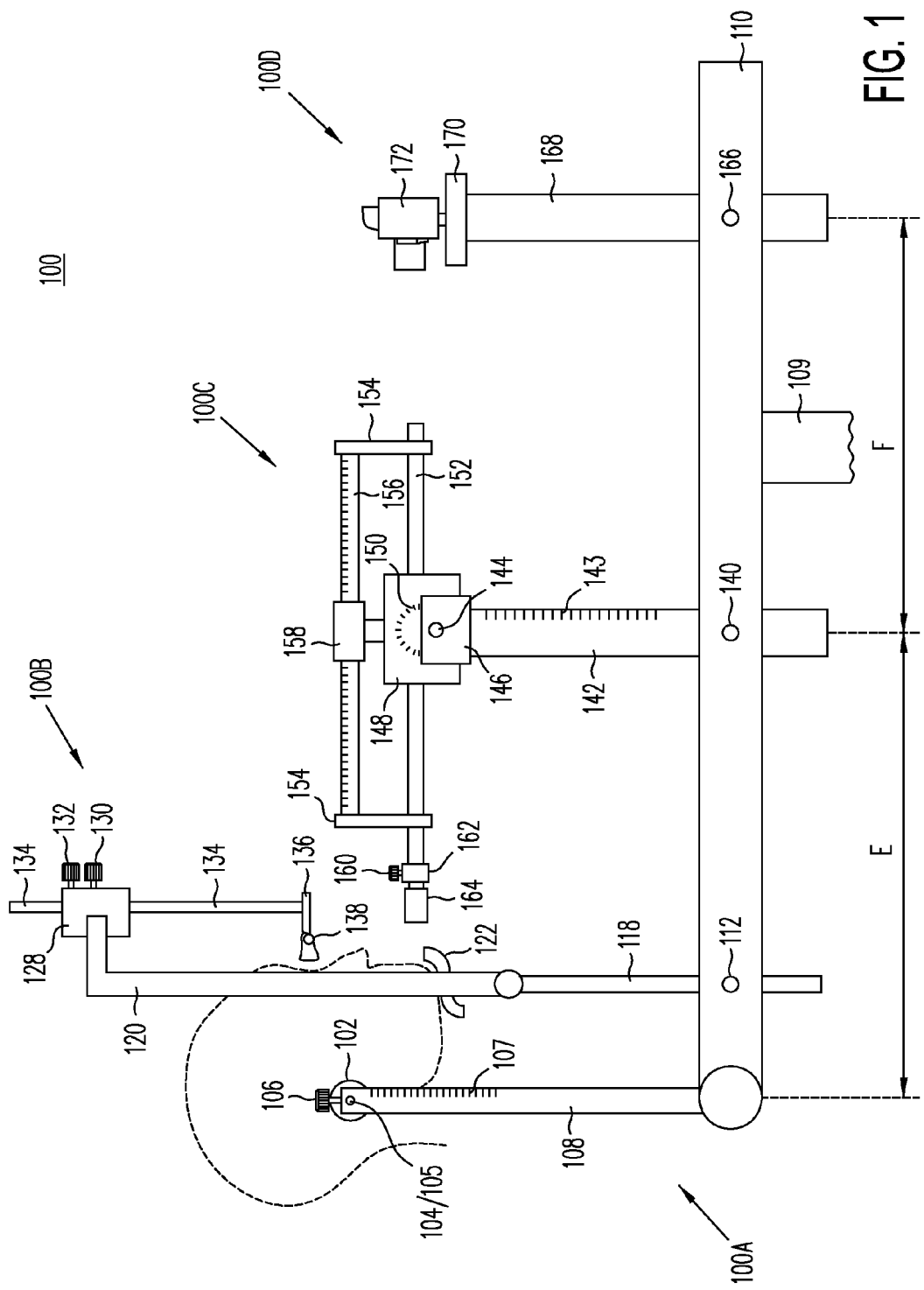
FIG. 1 is a side view of an embodiment of an apparatus for use in creating dental prosthetics.
Figure 2:
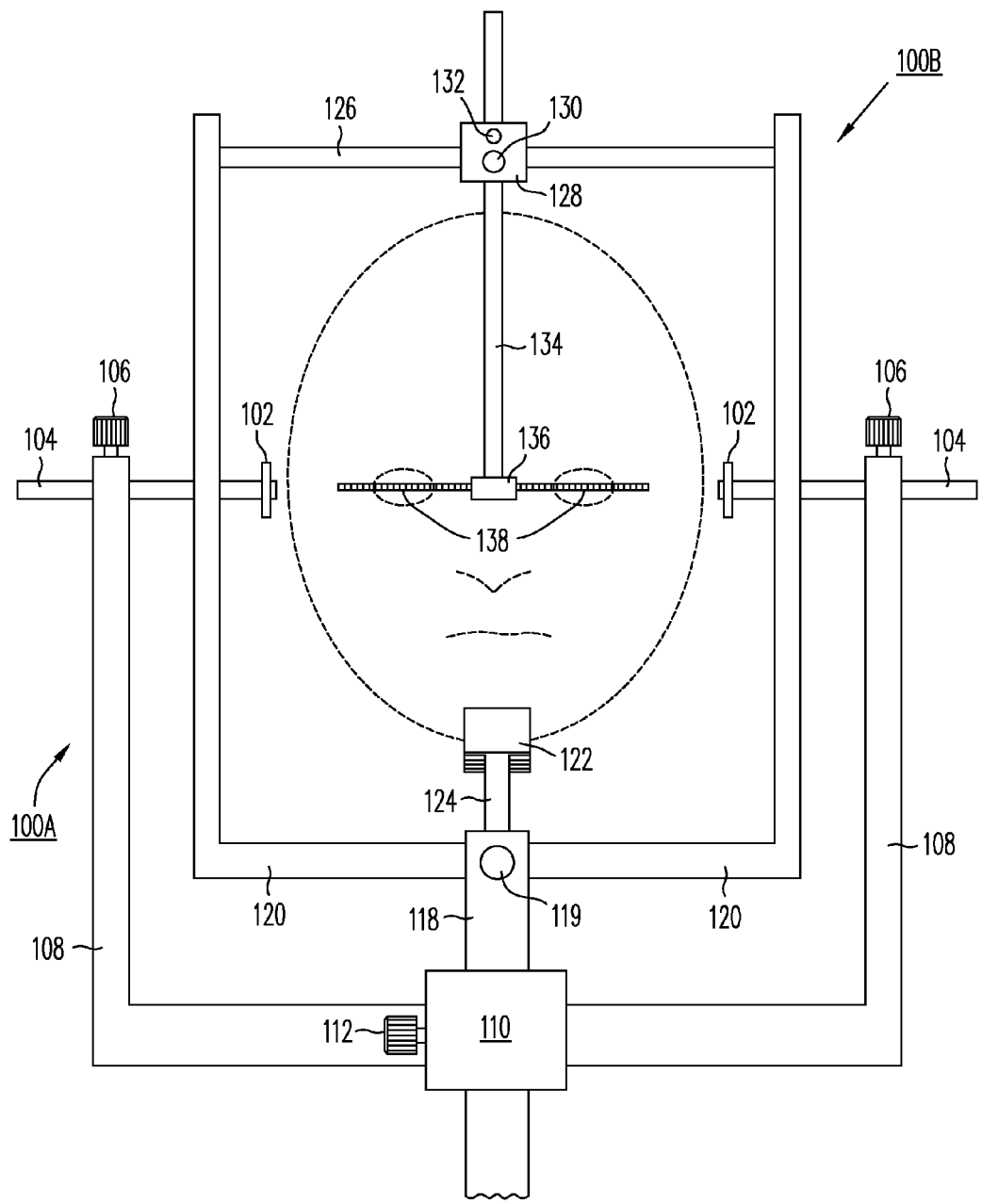
FIG. 2 is a view from the front end of the apparatus illustrated in FIG. 1.
Figure 3:
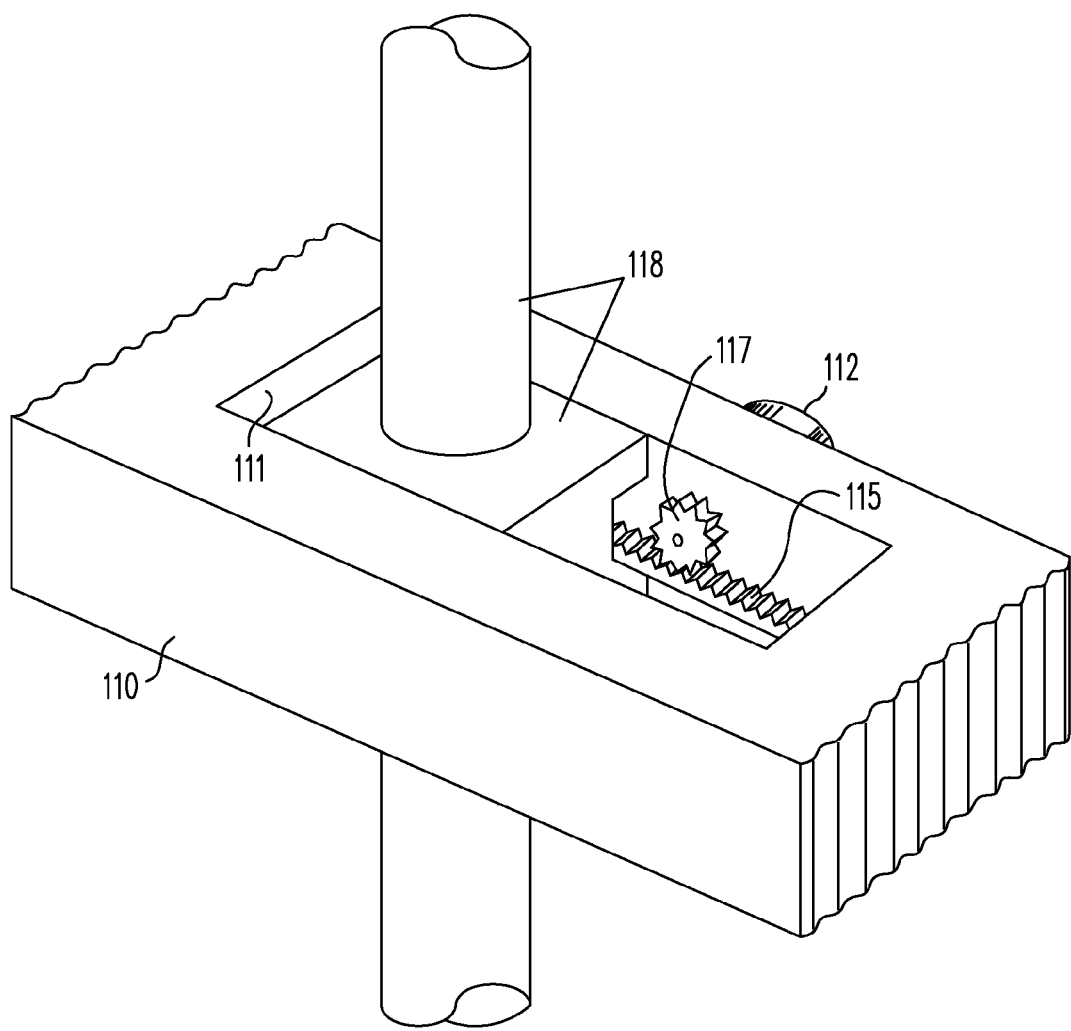
FIG. 3 is a perspective view of the base portion of the structure 100B illustrated in FIGS. 1 and 2.

In the following description specific details are set forth describing certain embodiments. It will be apparent, however, to one skilled in the art that the disclosed embodiments may be practiced without some or all of these specific details. The specific embodiments presented are meant to be illustrative, but not limiting. One skilled in the art may realize other material that, although not specifically described herein, is within the scope and spirit of this disclosure.

FIGS. 1 through 4B illustrate an apparatus 100 according to some embodiments for obtaining certain data for use in creating dental prosthetics for a particular patient, and FIGS. 5 through 9 illustrate a method for using the apparatus 100 to create a dental prosthesis according to some embodiments.

With reference to FIGS. 1 through 4B, the apparatus 100 comprises an ear mount portion 100A, a chin mount portion 100B, a bite fork portion 100C, and a camera mount portion 100D, each attached to a base 110. The ear mount portion 100A and chin mount portion 100B may be configured to fix a patient's head in position such that the patient's face is vertically and horizontally straight when viewed from the camera mount portion 100D, in a manner consistent from patient to patient, in order to obtain measurements of the patient's dental and facial information. The base 110 may be in the form of a bar or other generally straight, narrow and linear form, or a surface that is flat in two dimensions, with sufficient length to permit portions 100A-100D to be linearly mounted in relation to each other as described below. The base 110 is generally oriented horizontally and is fixedly mounted on a base mount 109 such that the base 110 is elevated from any surface on which the base mount 109 is fixed (such as the floor or a tabletop). Hereafter, this orientation of the base 110 is assumed, and the use of terms such as "upper" or "lower" is intended only to describe the relative spatial relationships of the various parts of the apparatus 100. The height or vertical position of the base 110 or the base mount 109 may additionally be adjustable, while maintaining the horizontal orientation of the base 110.

Consistent with some embodiments, the ear mount portion 100A may be U-shaped, and include two symmetrical and approximately curved or L-shaped ear mount arms 108 joined to form a single plane. The base of the ear mount portion 100A, where the two ear mount arms 108 join, is attached to one end of the base 110 such that the base 110 is orthogonal to the plane formed by the ear mount arms 108, and also such that in the normal orientation of the base 110, the non-attached ends of the ear mount arms 108 are perpendicular to and extend vertically upward. An earpiece rod 104 is inserted through a hole 105 in each non-attached end of each ear mount arm 108 such that the two rods 104 are collinear and parallel to the plane of the base 110. A scale 107 is affixed on each ear mount arm 108 so as to permit measurement of TMJ height, or the vertical distance from the patient's TMJ to the level of the patient's occlusal plane. An earpiece 102 is attached to the inward-pointing end of each earpiece rod 104. The position of the earpiece rods 104 may be adjusted by loosening screws 106 on each non-attached end of the ear mount arms 108, and may be fixed by re-tightening said screws 106, such that the earpieces 102 may be adjusted to contact a patient's ear canals. When the earpieces 102 are in contact with the patient's ear canals, the patient's head is thus fixed in position such that the patient's eyes are approximately level and equidistant from the base 110 and from the camera mount portion 100D.

The chin mount portion 100B is positioned on the base 110 between the ear mount portion 100A and the bite fork portion 100C, and is oriented so as to be parallel to the ear mount portion 100A and to extend in the same direction as the ear mount portion 100A from the base 110. The chin mount portion 100B is adjustably attached to the base 110 by means of an approximately rectangular-shaped chin mount post 118 inserted through a generally rectangular chin mount hole 111 in the base 110. The portion of the chin mount post 118 that is approximately within the chin mount hole 111 is preferably rectangular-shaped. The chin mount hole 111 is longitudinally larger in dimension than the chin mount post 118 such that the chin mount post 118 may be moved closer to or farther away from the ear mount portion 100A while inserted through the chin mount hole 111. In one embodiment, the horizontal movement of the chin mount post 118 may be controlled by adjustment gear 117 mounted on one side of the chin mount hole 111 and that makes contact with gear teeth 115. The gear teeth 115 are fixedly attached to the chin mount post 118 such that they extend longitudinally within the chin mount hole 111 and continuously contact the adjustment gear 117. Alternatively, the gear teeth 115 may be cut into a horizontal groove in one longitudinal side of the chin mount post 118 within the chin mount hole 111. The adjustment gear 117 is attached to an adjustment gear knob 112 such that the adjustment gear knob 112 turns the adjustment gear 117 and moves the chin mount post 118 horizontally toward or away from the ear mount portion 100A. Other means of controlling the horizontal movement of the chin mount post 118 such that the chin mount post 118 may be adjusted and then fixed into position may also be employed (e.g., the chin mount post 118 may be vertically fixed in position relative to the chin mount hole 111 by means of a tongue-and-groove assembly, and an adjusting plate may be used that, when loosened, permits the chin mount post 118 to be moved longitudinally, and when tightened, fixes the chin mount post 118 in a particular horizontal position relative to the ear mount portion 100A).

A chin rest post 124 is adjustably inserted into the upper end of chin mount post 118, and may be raised or lowered by loosening and tightening a chin rest tightener 119. Consistent with some embodiments, chin rest tightener 119 may be a screw, gear, or crank. A chin rest 122 is fixedly mounted on top of chin rest post 124. The height of the chin rest 122 and the horizontal position of the chin mount post 118 may be adjusted in order that the patient's chin rest upon the chin rest 122 while the patient's ear canals maintain contact with the earpieces 102. Two approximately curved or L-shaped chin mount arms 120 extend from either side of chin mount post 118, the upper ends of each chin mount arm 120 extending vertically upward such that the plane formed by the chin mount arms 120 is parallel with the plane formed by ear mount arms 108. The upper ends of the chin mount arms 120 protrude away from the plane of the ear mount arms 108 and chin mount arms 120, and are connected by a bar 126 that runs parallel to the two earpiece rods 104. A nosepiece rod 134 is adjustably attached to the bar 126 by means of a nosepiece rod joint 128 and is held in a vertical position by said nosepiece rod joint 128. The nosepiece rod 134 may be raised or lowered by means of loosening and tightening a screw 132, while the nosepiece rod joint 128 may be fixed at different points along bar 126 by means of loosening and tightening a screw 130. Attached to the bottom end of nosepiece rod 128 is a nosepiece 136 for making contact with the bridge of a patient's nose. The nosepiece 136 is positioned such that a line containing the contact point between the nosepiece 136 and the bridge of the patient's nose, and the contact point between the chin rest 122 and the patient's chin, is orthogonal to the base 110. Thus, when in contact with the nosepiece 136 and the chin rest 122, the patient's face is fixed in position such that the plane of the patient's face is orthogonal to the base 110. On either side of nosepiece 136 horizontally extend two eye measurement arms 138, and on each eye measurement arm 138 a measurement scale is provided (e.g., marked or printed) to be read when viewing the patient's face and such that the distance between the patient's pupils may be determined.

Figure 4A:
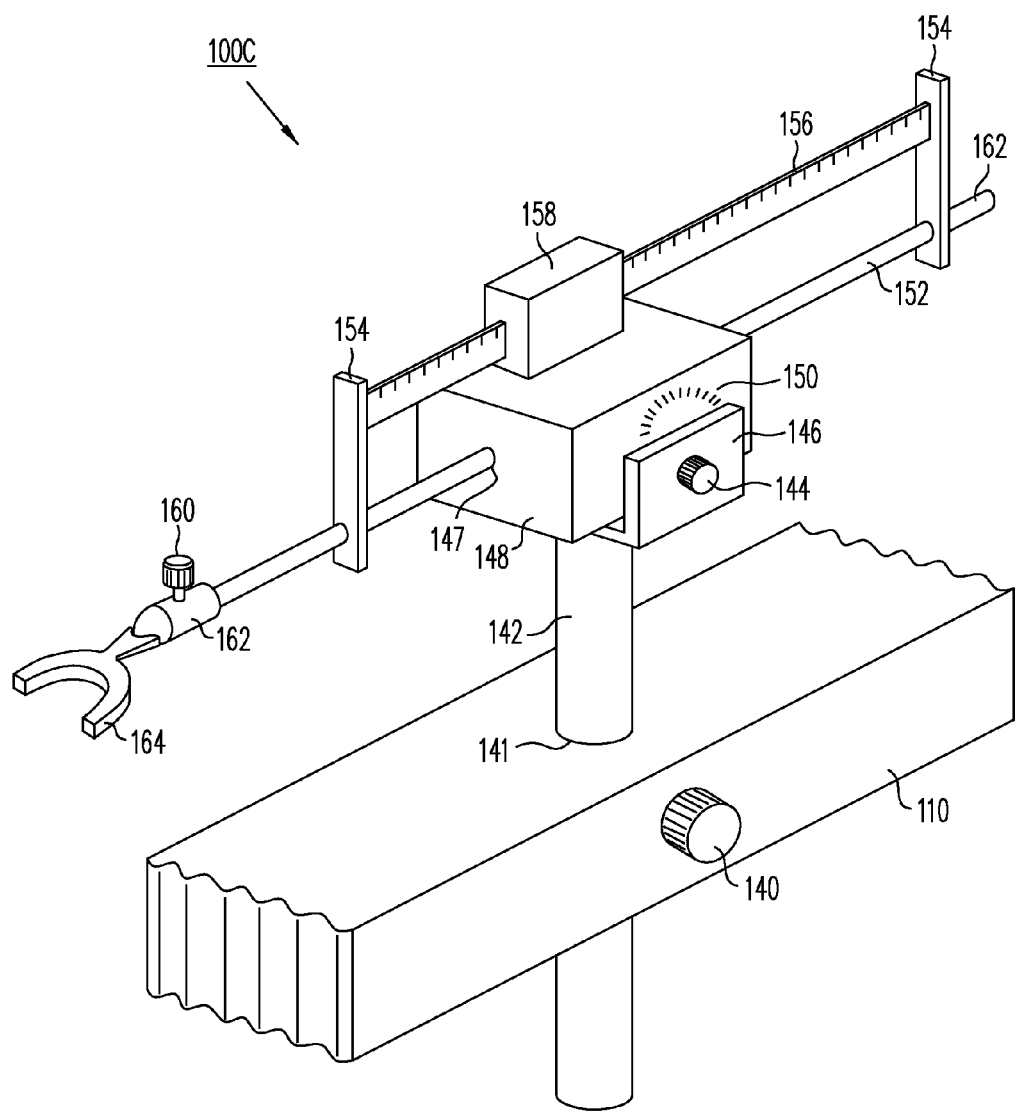
FIG. 4A is a perspective view of the structure 100C illustrated in FIG. 1.
Figure 4B:
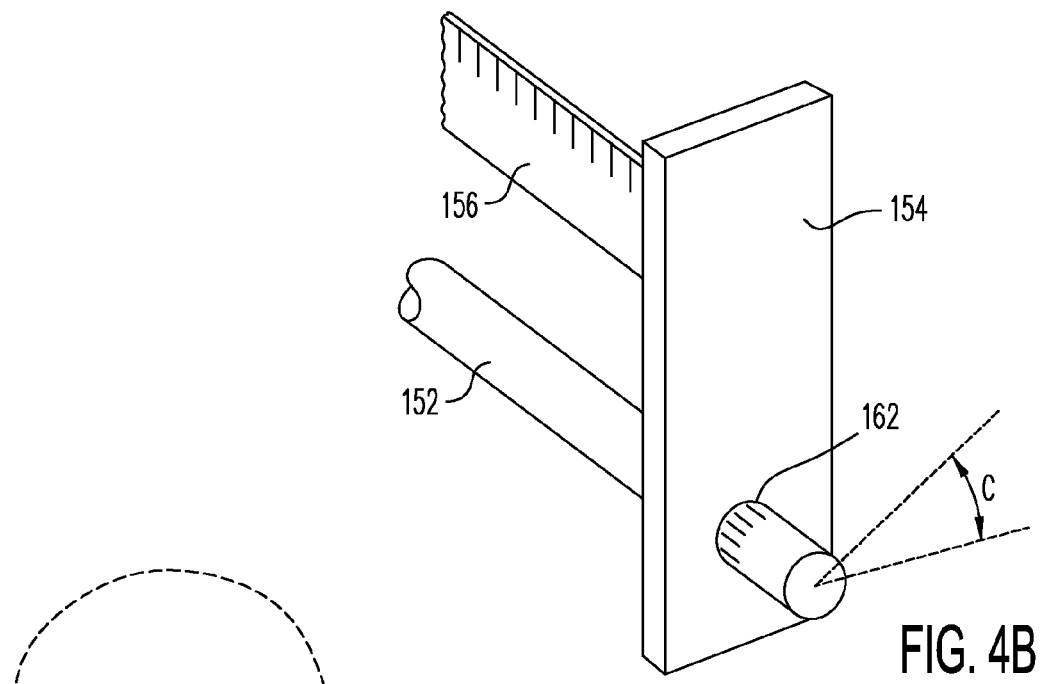
FIG. 4B is a reverse perspective view of the upper portion of structure 100C illustrated in FIG. 4A.
Figure 4C:
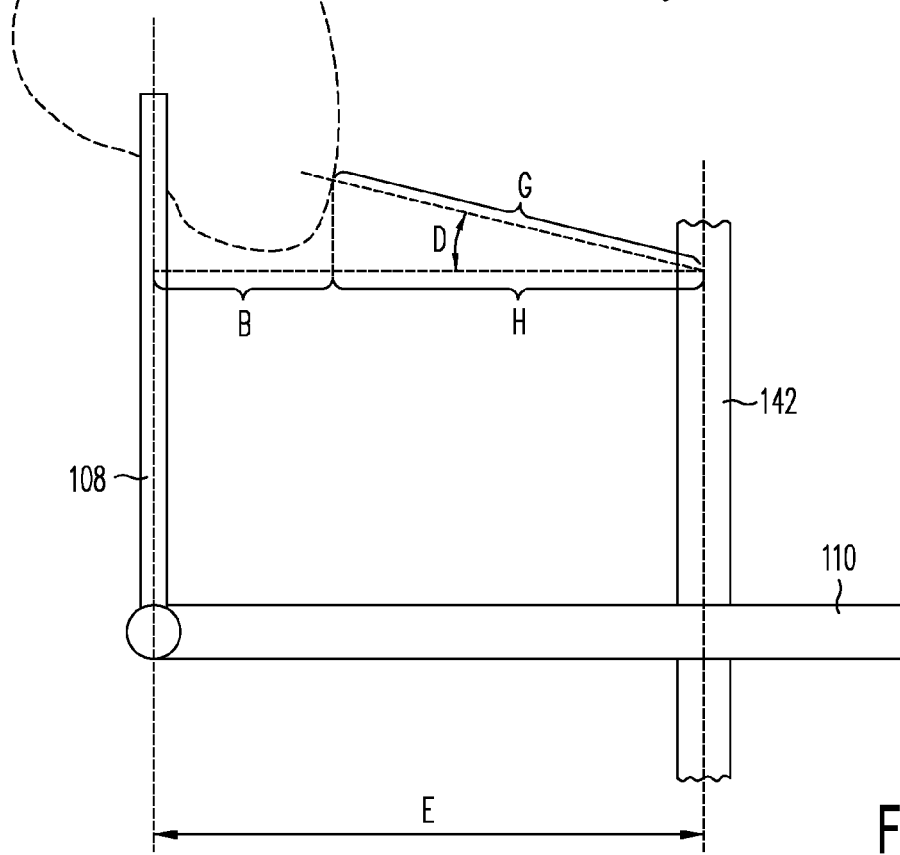
FIG. 4C is a side view of selected elements of the apparatus illustrated in FIG. 1 illustrating certain distances and angles measurable using the apparatus.

The bite fork portion 100C is positioned on the base 110 at a fixed horizontal distance from the ear mount portion 100A (and thus also at a fixed distance from the patient's TMJ) so as to accurately obtain the patient's bite registration once the patient's head is secured by the ear mount portion 100A and the chin mount portion 100B. A bite fork shaft 142 is adjustably inserted through a bite fork hole 141 in base 110 that is at a fixed distance E from the ear mount portion 100A. The bite fork shaft 142 may be raised or lowered through the bite fork hole 141 by means of loosening and tightening a tightener 140, which may be a screw, gear, or crank, thereby raising or lowering the bite fork portion 100C. A scale 143 is printed on the bite fork shaft 142 corresponding to the scale 107 on the ear mount arms 108, to permit the bite fork portion 100C to be raised or lowered to a specific height, for example corresponding to TMJ height. A bite fork cradle 146 is fixed to the upper end of the bite fork shaft 142. A bite fork mount 148 is attached to the bite fork cradle 146 by a bolt 144 so as to permit the bite fork mount 148 to rotate within the bite fork cradle 146 and to be fixed in position once a desired angle for the bite fork mount 148 is achieved. As depicted in FIG. 4A, an angular scale 150 is printed on a side(s) of the bite fork mount 148 where said mount 148 is attached to the bite fork cradle 146 by the bolt 144, so as to permit the angle of the bite fork mount 148 to be measured. Consistent with other embodiments, the angle of the bite fork mount 148 may be measured by a digital sensor rather than the angular scale 150, for example a digital sensor may be provided for measuring the rotation of the bolt 144. As illustrated in FIGS. 4A and 4C, the bite fork section 100C may be used to measure the front-to-back occlusal angle D of the patient's occlusal plane by raising or lowering the bite fork shaft 142 through the bite fork hole 141 and simultaneously tilting the bite fork mount 148 while the bite fork 164 is engaged in the patient's mouth until the bite fork 164 is positioned so as to match the front-to-back angle of the patient's occlusal plane. The front-to-back occlusal angle D may then be determined by using the scale 150 printed on the side of the bite fork mount 148, or, consistent with other embodiments, by measuring the angle of the bite fork mount 148 with a digital sensor. As illustrated in FIG. 4C, when the bite fork 164 is inserted into the patient's mouth to obtain the patient's bite registration, the distance G and the front-to-back occlusal angle D may be used to determine the horizontal distance H from the patient's anterior teeth to the bite fork shaft 142, and the TMJ-to-anterior distance B from the patient's TMJ to the patient's anterior teeth may thus be calculated by subtracting the distance H from the fixed distance E.

A bite fork mounting shaft 152 is adjustably inserted through a hole 147 extending through the two vertical sides of the bite fork mount 148 not directly attached to the bite fork cradle 146 by the bolt 144, so as to permit the bite fork mounting shaft 152 to be extended or retracted through the hole 147. A bite fork 164 is attached to one end of the bite fork mounting shaft 152, and the bite fork portion 100C is positioned such that the bite fork 164 is oriented toward the patient's face when held in place by the ear mount portion 100A and chin mount portion 100B. The bite fork cradle 146 and bite fork mount 148 are mounted on the bite fork shaft 142 such that when the height of the bite fork shaft 142 is fixed to correspond to the TMJ height, the bite fork mounting shaft 152 is parallel to the base 110 and the bite fork 164 is at the same vertical position as the patient's mouth.

A scale 156 is attached to the bite fork mounting shaft 152 by means of two mounting brackets 154 placed on either side of the bite fork mount 148, such that the scale 156 is parallel to the bite fork mounting shaft 152 and so as to permit the bite fork mounting shaft 152 to rotate within the mounting brackets 154 while maintaining the longitudinal position of the scale 156 relative to the bite fork mounting shaft 152. The scale 156 passes through a measuring device 158 which is fixed to the top of the bite fork mount 148, and is calibrated so as to measure the distance G along the bite fork mounting shaft 152 from the bite fork 164 to the center of the bite fork shaft 142. A mold or impression of the patient's teeth may also be obtained using the bite fork 164 in a manner similar to other commonly-used bite forks.

The bite fork 164 may be adjustably rotated along with the bite fork mounting shaft 152 to measure the left-to-right occlusal angle C of the occlusal plane of the patient's jaws around the axis formed by the bite fork mounting shaft 152, by loosening a bite fork mounting shaft screw 160 to permit rotation, and then tightening the bite fork mounting shaft screw 160 to fix the bite fork mounting shaft 152 and the bite fork 164 in place. As depicted in FIG. 4B, a scale 162 may be provided (e.g., printed) on or around the bite fork mounting shaft 152 in order to measure said left-to-right occlusal angle C. Consistent with other embodiments, the left-to-right occlusal angle C may be measured using a digital sensor instead of scale 162, for example a digital sensor for measuring the rotation of bite fork mounting shaft 152.

The camera mount portion 100D positioned on the base 110 at a fixed horizontal distance away from the ear mount portion 100A that is further from said ear mount portion 100A than the bite fork portion 100C. A camera mount shaft 168 is adjustably inserted through a camera mount hole 165 in base 110 that is at a fixed distance F from the ear mount portion 100A. The camera mount shaft 168 may be raised or lowered through the camera mount hole 165 by means of loosening and tightening a tightener 166, which may be a screw, gear, or crank, thereby raising or lowering the camera mount portion 100D. A camera mount 170 is fixed to the upper end of the camera mount shaft 168, where a camera 172 may be attached such that an image may be taken of the patient's face while set in the ear mount portion 100A and chin mount portion 100B. To ensure the consistency of images from patient to patient, the camera mount shaft 168 is raised or lowered such that the tip of the patient's nose is centered in the viewfinder of camera 172.

With reference to FIGS. 1 through 10, the following method may be used to obtain measurements and information from a patient for the purpose of preparing dental prosthetics of the correct visual appearance and proportions. A patient's head is positioned on the apparatus 100 such that the ear pieces 102 may be adjusted to fit into the patient's ear canals, and the patient's chin may simultaneously rest on the chin rest 122 after adjusting the chin mount post 118 and the chin rest post 124. The patient's head thus should be approximately horizontally centered between the ear mount arms 108 and the chin mount arms 120 when viewed from the front. The nosepiece rod joint 128 and the nosepiece rod 134 are then adjusted such that the nosepiece 136 makes contact with the patient's upper nose and is centered between the patient's eyes. Once all four contact points between the apparatus 100 and the patient's head are established (each ear canal, chin, and nose), the patient's head is properly positioned to obtain the required measurements for preparing a dental prosthesis.

The patient's bite registration is then taken. The height of the bite fork portion 100C is adjusted to match the TMJ height as measured on the ear mount arms 108, such that the bite fork 164 is at the same vertical height as the patient's mouth. The bite fork mounting shaft 152 is extended toward the patient's mouth such that the patient is able to bite down on the bite fork 164. The bite fork mounting shaft 152 is twisted as necessary to match the left-to-right angle of the patient's occlusal plane, and the angle of the bite fork mount 148 and the height of the bite fork shaft 142 are adjusted as necessary to match the front-to-back angle of the patient's occlusal plane. Once the bite fork 164 is correctly positioned in the patient's mouth, the TMJ-to-anterior distance B is obtained using the scale 156, the left-to-right occlusal angle C is obtained using the angular scale 150, and the front-to-back occlusal angle D is obtained using the scale 162.

Once these measurements are taken, the bite fork portion 100C may be removed from the base 110. The bite fork portion 100C is then positioned relative to a dental articulator such that the bite fork 164 is correctly positioned within the dental articulator to permit the patient's dental models to be mounted to the articulator in the proper spatial orientation. Alternatively, the measurements are recorded and transmitted to a dental lab for use in positioning a second bite fork portion 100C relative to an articulator. As dental articulators are generally designed to replicate the position of a patient's jaws relative to the TMJ, and as the TMJ height and the TMJ-to-anterior distance B of the patient have been obtained as described above, it is thereby possible for one skilled in the art to establish the proper relative positions of the articulator and the bite fork 164, such as by fixing the bite fork portion 100C in place and adjusting the position of the articulator relative to the bite fork portion 100C consistent with the patient's measurements, or vice versa.

The bite fork portion 100C is also removed from the base 110 in order to permit an image to be taken of the patient's face while still set within the apparatus 100. The camera mount shaft 168 is adjusted such that the viewfinder of the camera 172 mounted to the camera mount 170 is centered on the patient's nose tip. Once the camera 172 is in the correct position, the patient is directed to smile so as to expose the patient's upper teeth, and the image is taken. The correct shape of the patient's dental prosthetics may be determined with reference to the image as follows.

Figure 5:
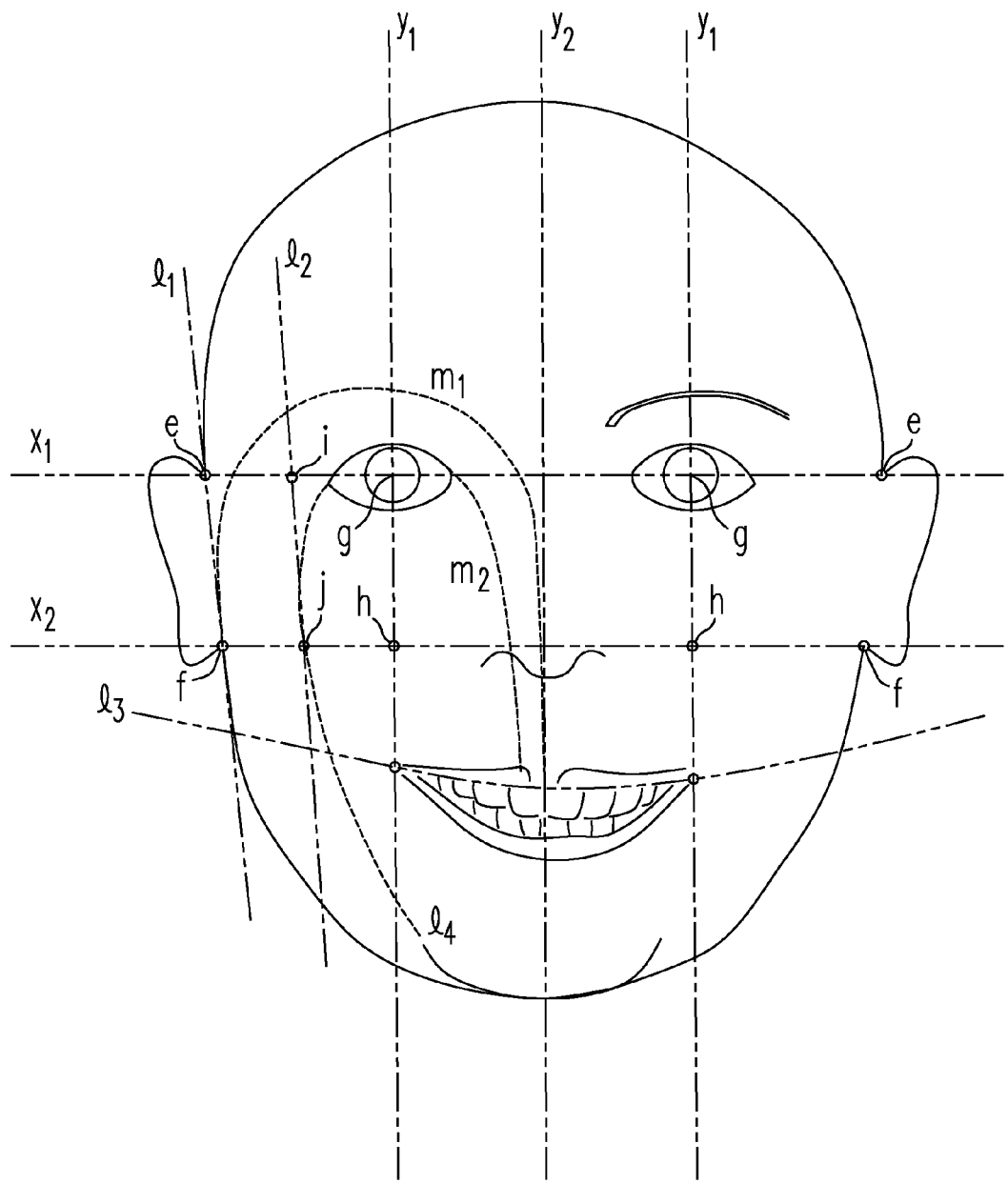
FIG. 5 is a diagram of reference lines overlaid on a frontal view of a patient's face used in an embodiment of a method for use in creating dental prosthetics.

The following steps of the claimed method, as shown in FIGS. 5 through 10, will be described with reference to one side of the image of the patient's face only, corresponding to the anterior teeth (i.e., teeth numbers 6 through 11 and 22 through 27) on the same side of the patient's face. However, the patient's face is assumed to be approximately symmetrical, and thus the claimed method may be applied in reverse on the other side of the patient's face to correspond to the anterior teeth on that side also, according to some embodiments. As shown in FIG. 5, an upper ear line $x_1$ is horizontally traced on the image through the two points e where the patient's upper ears join with the patient's head. A lower ear line $x_2$ is horizontally traced on the image through the two points f where the patient's lower ears join with the patient's head. An eye-mouth line $y_1$ is vertically traced through the patient's pupil and the corner of the patient's mouth, such that the eye-mouth line $y_1$ intersects with the upper ear line $x_1$ at point g, and with the lower ear line $x_2$ at point h. A face center line $y_2$ is vertically traced through the image so as to bisect the patient's face.

Once the above points and lines are drawn, the following reference lines may be determined. A face outline $l_1$ is drawn through point e and point f so as to form a line approximately tangential to the patient's face. A face line $l_2$ is drawn through a point i, located on the upper ear line $x_1$ midway between point e and point g, and a point j, located on the lower ear line $x_2$ midway between point f and point h. An upper lip line $l_3$ is drawn along the curve formed by the two corners of the patient's mouth and the lower edge of the center of the patient's upper lip (while smiling) so as to form a curved line extending to either side of the patient's face. The upper lip line $l_3$ corresponds to the patient's incisal line. A chin angle line $l_4$ is drawn along the curve formed by the contour of the patient's depressor anguli oris or triangularis muscle and the patient's chin.

Using the above reference lines, the proper shape of the patient's upper anterior teeth may be determined as follows. A tooth outline $m_1$ is determined by tracing a curved line beginning at the upper lip line $l_3$ at the center of the patient's upper lip, extending vertically through the lower part of the patient's nose, curving outward to correspond to the patient's eyebrow, curving downward and outward so as to meet and overlap the face outline $l_1$, and continuing downward to contact the upper lip line $l_3$ once again. The disto-labial angle of the tooth outline $m_1$ (i.e., the lower outer corner of the tooth outline $m_1$, or the lower corner farthest from the patient's nose) is then adjusted to correspond to the curvature of the chin angle line $l_4$. The resulting outline formed by the tooth outline $m_1$, upper lip line $l_3$, and adjusted lower corners approximately corresponds to the proper outline of the patient's upper anterior teeth when frontally viewed.

A tooth contour line $m_2$ is determined by tracing a curved line beginning at a point on the upper lip line $l_3$ that is slightly laterally offset from the center of the patient's teeth, extending vertically through the lower part of the patient's nose, curving outward to correspond to the upper edge of the patient's eye, curving downward and outward to contact the face line $l_2$, and then curving downward to contact the upper line line $l_3$ on a curve approximately corresponding to the patient's depressor anguli oris or triangularis muscle. The resulting tooth contour line $m_2$ approximately corresponds to the contour on the facial surface of the patient's upper anterior tooth where the facial surface transitions into the proximal and gingival surfaces of the tooth.

Figure 6:
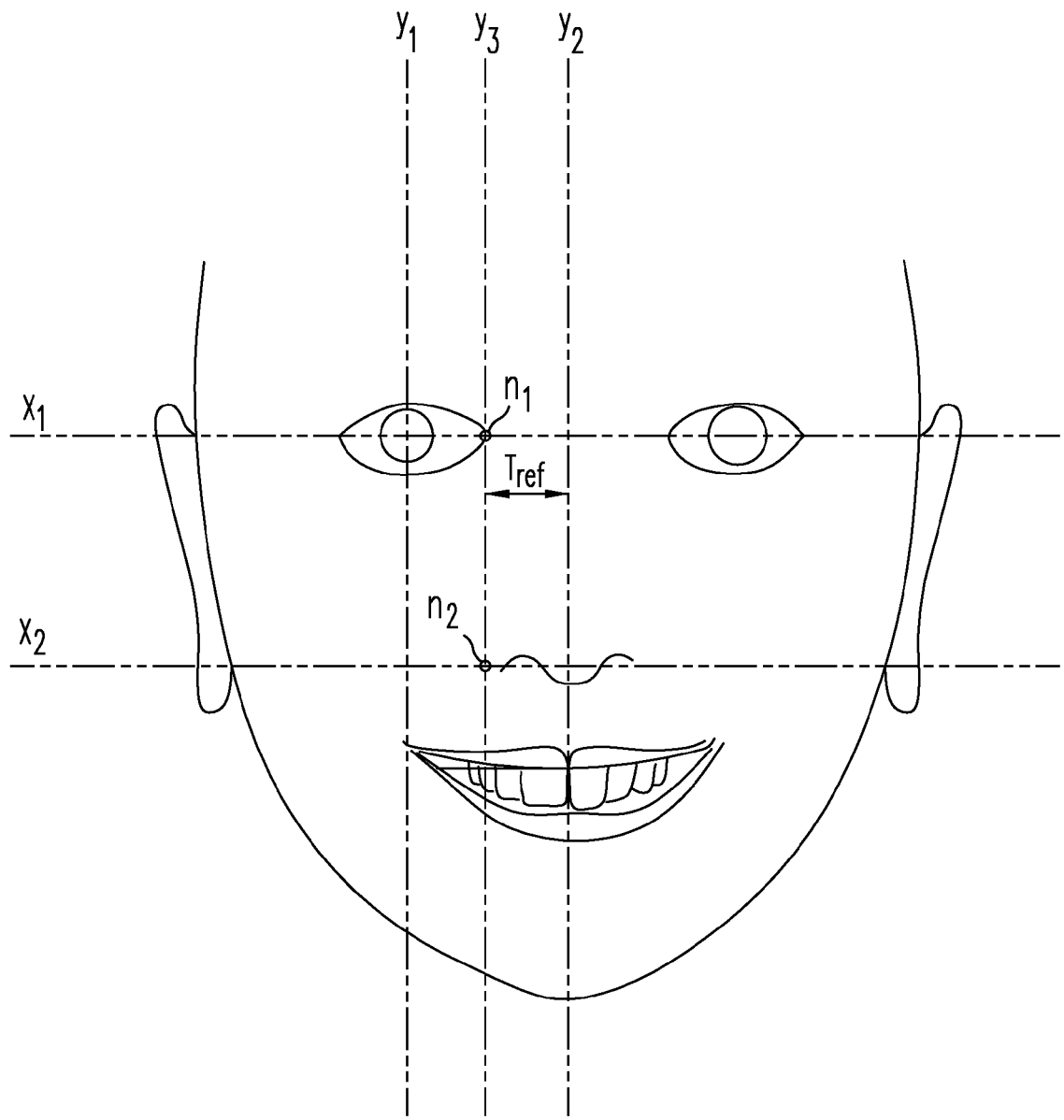
FIG. 6 is a diagram of reference lines overlaid on a frontal view of a patient's face used in an embodiment of the method of FIG. 5.

The proper size of the patient's visible upper teeth (i.e., tooth numbers 4 through 13) may be determined as follows. With reference to FIG. 6, a point $n_1$ is located on upper ear line $x_1$ halfway between eye-mouth line $y_1$ and face center line $y_2$. A point $n_2$ is similarly located on lower ear line $x_2$ halfway between eye-mouth line $y_1$ and face center line $y_2$, on the same side of the patient's face as point $n_1$. A canine line $y_3$ is vertically traced through point $n_1$ and point $n_2$, and should approximately intersect with the cusp of the patient's canine or cuspid tooth (i.e., tooth number 6 or 11). Thus, the distance $T_{ref}$ between point $n_1$ and face center line $y_2$ should correspond to the horizontal distance from the center of the patient's upper teeth (i.e., between tooth numbers 8 and 9) and the cusp of the patient's canine tooth.

A width $T_1$ of each of the patient's central upper incisors (i.e., tooth numbers 8 and 9) may be determined as follows. Due to the curvature of the maxillary arch, each subsequent lateral tooth from the central incisors has an apparent frontal width (i.e., width when viewed from the front) of three-quarters the apparent frontal width of the immediately mesial tooth. For example, each lateral incisor (i.e., teeth number 7 and 10) has an apparent frontal width $T_2$ equivalent to $0.75*T_1$. Each canine tooth (i.e., teeth number 6 and 11) has an apparent frontal width $T_3$ equivalent to $0.75*T2$ or $0.75*(0.75*T_1)$. Similarly, each of teeth number 5 and 12 has an apparent frontal width $T_4$ equivalent to $0.75*T_3$ or $0.75*(0.75*(0.75*T_1))$, and each of teeth number 4 and 13 has an apparent frontal width $T_5$ equivalent to $0.75*T_4$ or $0.75*(0.75*(0.75*(0.75*T_1)))$. The width of each subsequent lateral tooth may be determined in a similar fashion. The distance $T_{ref}$ being known, the width $T_1$ thus may be calculated according to the equation $T_1 = T_{ref} - T_2 - (0.5)T_3$.

Figure 7A:
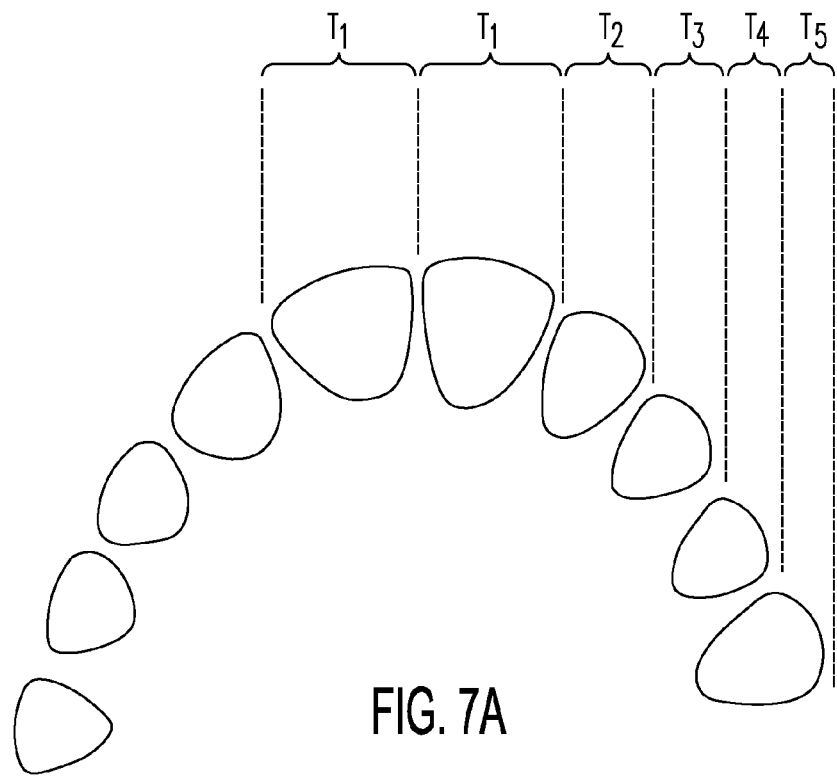
FIG. 7A is a diagram of reference lines overlaid on a planar view of a patient's teeth used in an embodiment of the method of FIG. 5.
Figure 7B:
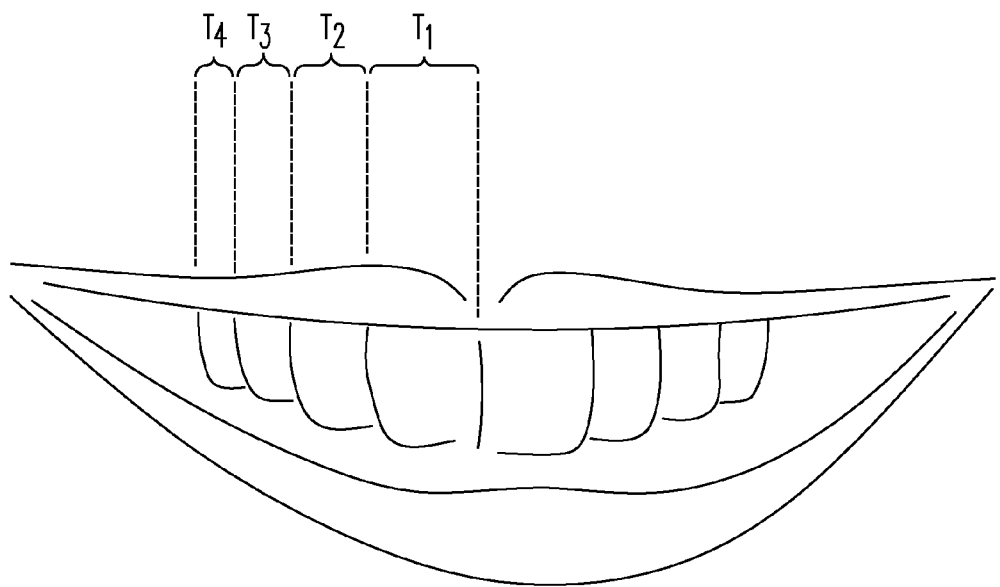
FIG. 7B is a diagram of reference lines overlaid on a frontal view of a patient's teeth used in an embodiment of the method of FIG. 5.

The placement and width of each remaining visible upper tooth may be determined by reference to the apparent frontal width of each visible upper tooth and each tooth's placement on the patient's maxillary arch, as shown in FIGS. 7A and 7B. The proper height of each tooth is approximately 1.24 times the width of the tooth.

Figure 8:
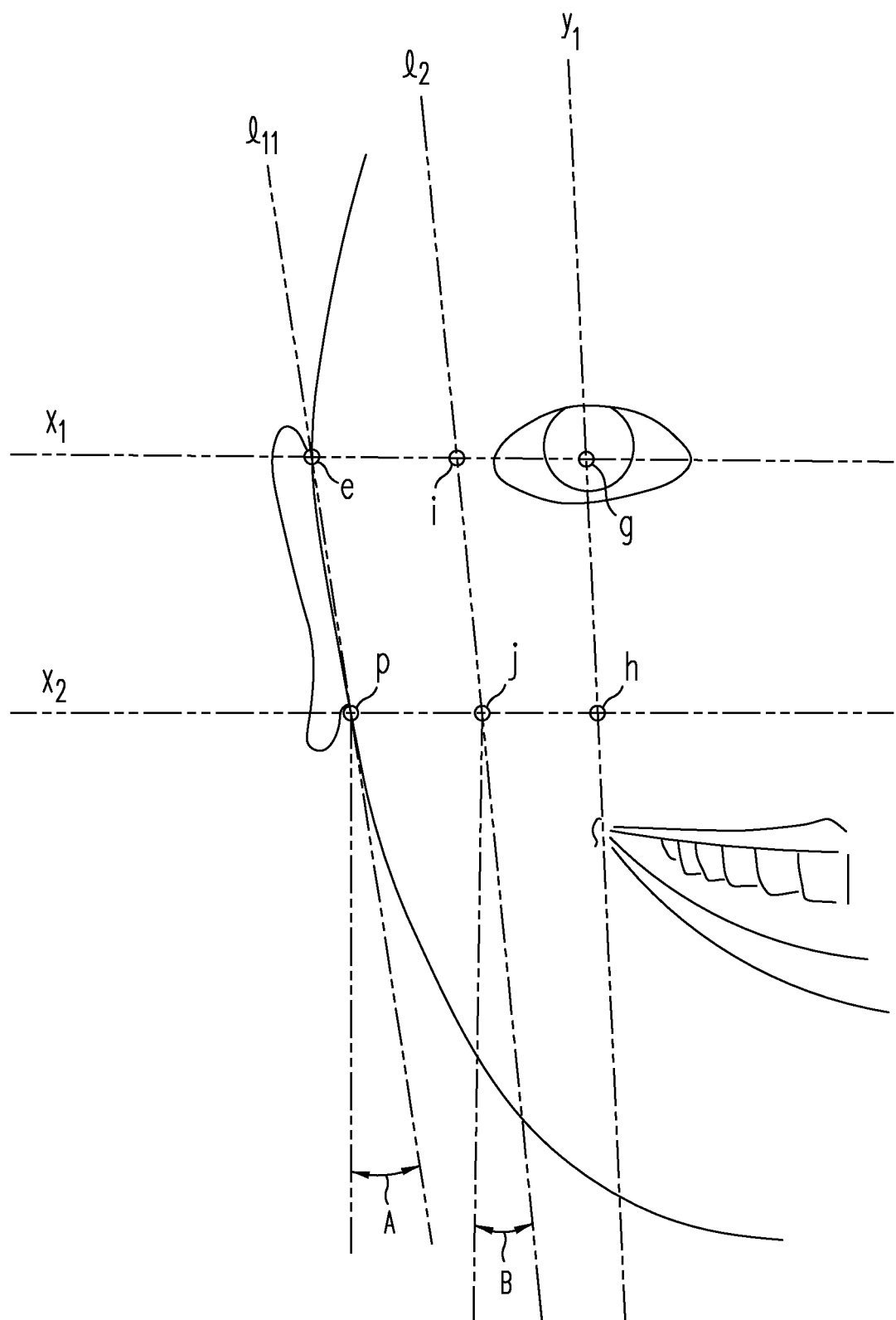
FIG. 8 is a diagram of reference lines overlaid on a frontal view of a patient's face used in an embodiment of the method of FIG. 5.
Figure 9:
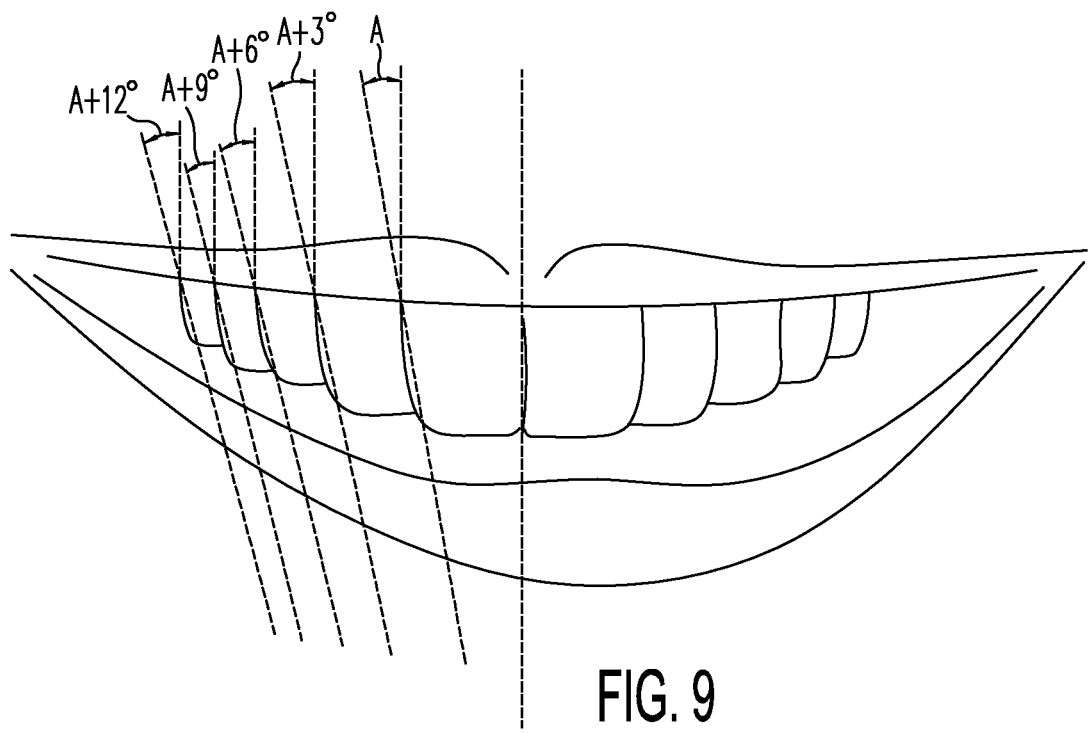
FIG. 9 is a diagram of reference lines overlaid on a frontal view of a patient's teeth used in an embodiment of the method of FIG. 5.

The angle of each visible upper tooth when frontally viewed may be determined as follows. With reference to FIGS. 5, 8 and 9, as explained above, the outer edge of the tooth outline $m_1$ largely overlaps the face outline $l_1$. The face outline $l_1$ generally has an angle A from the vertical, as shown in FIG. 8. Thus, the outer edge of the patient's central upper incisors should be angled at approximately the same angle A as the face outline $l_1$. The angle of each subsequently lateral tooth should be 3 degrees greater than the immediately mesial tooth, as shown in FIG. 9. That is, the angle of the lateral incisor should be angle A plus 3 degrees, the angle of the canine or cuspid tooth should be angle A plus 6 degrees, and so on.

The angle of the tooth contour as represented by the tooth contour line $m_2$ is similarly calculated. The face line $l_2$, corresponding to the outer edge of the tooth contour as represented by tooth contour line $m_2$, generally has an angle B from the vertical, as shown in FIG. 8. The outer edge of the tooth contour of the patient's central upper incisors should be angled at approximately the same angle B as the face line $l_2$. The angle of the tooth contour of each subsequently lateral tooth should be 3 degrees greater than the immediately mesial tooth, in a manner similar to that described in FIG. 9 with respect to angle A.

Figure 10:
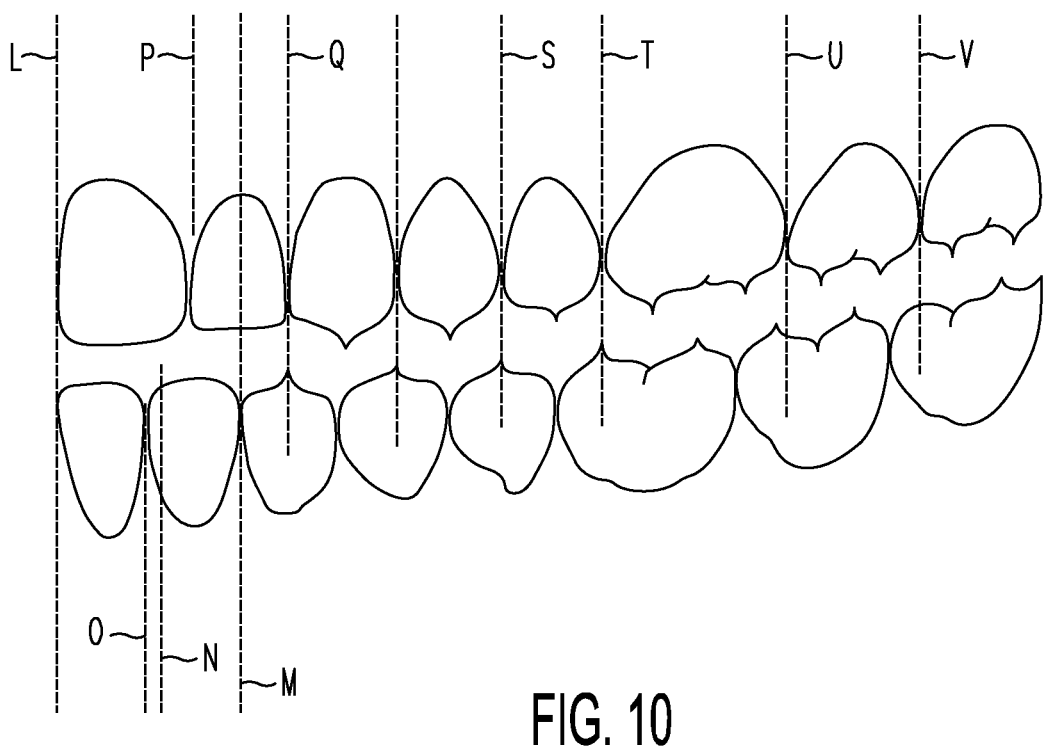
FIG. 10 is a diagram of reference lines overlaid on an approximately frontal representation of a patient's teeth use in an embodiment of the method of FIG. 5.

With reference to FIG. 10, the proper proportions of the patient's lower teeth may be determined by reference to the patient's upper teeth. Line L corresponds to the center line between the patient's central incisors. Line M corresponds to the outer edge of the lower lateral incisor (i.e., tooth number 23 or 26 depending on which side of the patient's face is being viewed). The placement of line M also corresponds to the center of the patient's lateral upper incisor (i.e., tooth number 7 or 10). Line N is located halfway between lines L and M, and approximately corresponds to the gap between the patient's lower central and lateral incisors. However, the lower central incisor is generally approximately 1 mm narrower than the lower lateral incisor, and so the outer edge of the lower central incisor and the inner edge of the lower lateral incisor meet at a line O located ½ mm from line N in a mesial direction. A line P corresponding to the gap between the patient's central and lateral upper incisors should approximately intersect with the center of the patient's lower lateral incisor. Lines Q through V, corresponding to the remaining gaps between the patient's upper teeth, should each approximately correspond to the cusp tip of the lower tooth located below each such gap. In this way, the size and placement of each of the patient's lower teeth may be determined.

Although a few embodiments have been shown and described, it will be appreciated by those skilled in the art that changes may be made in these embodiments without departing from the principles and spirit of the disclosure, the scope of which is defined in the appended claims and their equivalents.

What is claimed is:

1. An apparatus for use in creating dental prosthetics, comprising:
    an ear mount portion including ear-mount arms that extend in a first direction and are configured to contact a patient's head such that temporomandibular joints within the patient's head are maintained in a level fixed position, the ear mount portion connects to a base at a first fixed point along the base;
    the base extending in a second direction that is orthogonal to the first direction;
    a chin mount portion having a chin rest configured to contact the patient's chin and a nose piece configured to contact the patient's nose bridge, such that the chin rest and the nose piece align along a third direction that is perpendicular to the first direction and the second direction, the chin mount portion connects to the base at a variable point along the base between the first fixed point and a second fixed point;
    a bite fork portion comprising a bite fork which may be inserted into the patient's mouth for the purpose of obtaining bite registration information of the patient, the bite fork portion connects to the base at the second fixed point along the base; and
    a camera mount portion comprising a camera oriented toward the patient's face, the camera mount portion connects to the base at a third fixed point along the base such that the second fixed point lies between the first and third fixed points,
    wherein the base includes a first mechanism that adjusts and maintains the variable point along a length of the base, a second mechanism that adjusts the height of the bite fork portion in relation to the base, and a third mechanism that adjusts the height of the camera mount portion in relation to the base.

2. The apparatus of claim 1, wherein the bite registration information comprises at least a front-to-back occlusal angle of an occlusal plane of the patient, a left-to-right occlusal angle of the occlusal plane, and a horizontal distance from the patient's temporomandibular joint to the patient's anterior teeth, and an angular position, rotational position, and vertical position of the bite fork is adjustable such that the bite fork may be positioned so as to approximately correspond to the occlusal plane of the patient.

3. The apparatus of claim 2, where the bite fork portion is removable from the base and may be positioned relative to a dental articulator so as to correspond to the patient's bite registration information.

4. The apparatus of claim 3, further comprising a scale for measuring the distance between the patient's pupils.

5. A method for creating dental prosthetics, comprising:
    using an ear mount portion to maintain a patient's temporomandibular joints in a fixed position, the ear mount portion having ear-mount arms that extend in a first direction;
    maintaining the patient's nose bridge and chin in a fixed orientation relative to a base, a bite fork and a camera, wherein:
        the base extends in a second direction perpendicular to the first direction;
        the patient's eyes are level and equidistant from the camera;
        the patient's nose bridge and chin are perpendicularly oriented relative to the base and the ear-mount arms; and
        the camera is centered on the patient's nose;
    obtaining a bite registration of the patient;
    obtaining a photograph of the patient's face;
    determining a proper shape of one or more dental prostheses by:
        determining a face outline that corresponds to a line intersecting the two points in the photograph where the upper and lower parts of the patient's ear attach to the patient's head, determining a face line that corresponds to a line intersecting a point horizontally equidistant from the patient's upper ear attach point and the patient's pupil and a point horizontally equidistant from the patient's lower ear attach point and the patient's pupil, determining an upper lip line that corresponds to a curved line that overlaps and approximately extends from a curve of the patient's upper lip when smiling, and determining a chin angle that corresponds to a curved line that overlaps and approximately extends from a curve of the patient's depressor anguli oris or triangularis muscle; and creating the one or more dental prostheses based upon information from the bite registration and measurements obtained from the photograph of the patient's face.

6. The method of claim 5, wherein the photograph of the patient's face is obtained using the camera to take an image from a frontal perspective, and the patient's bite registration is obtained using the bite fork.

7. The method of claim 5, wherein the patient's head, the bite fork, and the camera are maintained at fixed horizontal distances from each other.

8. The method of claim 7, wherein obtaining the photograph includes photographing a scale for measuring the distance between the patient's pupils.

9. The method of claim 8, wherein determining a proper shape of the one or more dental prostheses includes referencing a set of contours obtained from one side of the patient's face.

10. The method of claim 5, wherein the proper shape comprises a tooth outline approximately corresponding, in an upper part, to a curved line beginning from the center of the patient's upper lip, extending vertically through the patient's nose, curving outwards so as to overlap the patient's eyebrow, and curving downwards so as to tangentially contact the face outline, and in a lower part, to a curved line corresponding to the upper lip line.

11. The method of claim 10, wherein the proper shape further comprises a tooth contour approximately corresponding to the chin angle, tangentially contacting the face line, curving inwards so as to overlap an upper contour of the patient's eye, and extending downwards so as to intersect the patient's upper lip at a point laterally offset from the center of the upper lip.

12. The method of claim 11, further comprising determining a size of one or more upper dental prostheses of the one or more dental prostheses, wherein half a horizontal distance between the patient's pupil and a center of the patient's nose is equivalent to a horizontal distance from a boundary between two upper front teeth to the cusp of one of the patient's canine teeth, and a frontal width of a lateral incisor is 0.75 times the frontal width of a central upper incisor.

13. The method of claim 12, further comprising determining an angle of the one or more upper dental prostheses of the one or more dental prostheses, wherein an angle between a vertical line and a tooth outline of the patient's central upper incisor tooth is equivalent to an angle between a vertical line and a line through the patient's upper ear attach point and the patient's lower ear attach point, with the angle of each subsequently lateral tooth outline progressively increased by 3 degrees.

14. The method of claim 13, further comprising determining a size of one or more lower dental prostheses of the one or more dental prostheses, wherein a width of a lower incisor tooth is one millimeter smaller than one-half the combined width of a lower incisor and a lower lateral incisor tooth, and a gap between two of the patient's upper teeth corresponds to a cusp of the patient's lower tooth.

* * * * *